US006200783B1

(12) United States Patent
Chaen et al.

(10) Patent No.: US 6,200,783 B1
(45) **Date of Patent: *Mar. 13, 2001**

(54) PROCESS FOR PRODUCING TREHALOSE AND SUGAR ALCOHOLS

(75) Inventors: Hiroto Chaen; Takashi Shibuya; Shigeharu Fukuda, all of Okayama (JP)

(73) Assignee: Kabushiki Kaisha Hayashibara Seibutsu Kagaku Kenkyujo, Okayama (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/157,107

(22) Filed: Sep. 18, 1998

(30) Foreign Application Priority Data

Oct. 16, 1997 (JP) ........................................ 10-297957

(51) Int. Cl.[7] ........................................ C12P 19/12

(52) U.S. Cl. .................... 435/100; 435/101; 536/123.13; 536/127; 210/690; 210/691; 210/692

(58) Field of Search ................................ 536/127, 123.1; 435/100, 101; 210/692, 691, 690

(56) References Cited

FOREIGN PATENT DOCUMENTS

| | | |
|---|---|---|
| 0606753 | 7/1994 | (EP) . |
| 0619951 | 10/1994 | (EP) . |
| 0628630 | 12/1994 | (EP) . |
| 0636693 | 2/1995 | (EP) . |
| 0671470 | 9/1995 | (EP) . |
| 0688866 | 12/1995 | (EP) . |
| 0690130 | 1/1996 | (EP) . |
| 0693558 | 1/1996 | (EP) . |
| 0695804 | 2/1996 | (EP) . |
| 0697461 | 2/1996 | (EP) . |
| 0704531 | 4/1996 | (EP) . |
| 0 794 259 | 9/1997 | (EP) . |
| 47-13699 | 4/1972 | (JP) . |
| 58-216695 | 12/1983 | (JP) . |
| 4-26817 | 5/1992 | (JP) . |
| 6-319486 | 11/1994 | (JP) . |
| 7-143876 | 6/1995 | (JP) . |
| 7-170977 | 7/1995 | (JP) . |
| 7-213283 | 8/1995 | (JP) . |
| 7-298880 | 11/1995 | (JP) . |
| 8-263 | 1/1996 | (JP) . |
| 8-66186 | 3/1996 | (JP) . |
| 8-73482 | 3/1996 | (JP) . |
| 8-149980 | 6/1996 | (JP) . |
| 8-336388 | 12/1996 | (JP) . |
| 9-9986 | 1/1997 | (JP) . |

OTHER PUBLICATIONS

Database WPI; Section Ch, Week 198828; Derwent Publications Ltd.; London, GB; Class B03, AN 1988–193405; XP002146393, and JP 63129990 A (Mitsui Sugar Co. Ltd.); Jun. 2, 1988; Abstract.

Database WPI; Section Ch, Week 199304; Derwent Publications Ltd.; London, GB; Class D16, AN 1993–032619; XP002146394, and JP 04 360692 A (Kaneka Corp.); Dec. 14, 1992; Abstract.

Database WPI; Section Ch, Week 198848; Derwent Publications Ltd.; London, GB; Class D16, AN 1998–560717; XP002146392, and JP 10 248560 A (Nippon Shokuhin Kako KK) Sep. 22, 1998; Abstract.

*Primary Examiner*—Francisco Prats
(74) *Attorney, Agent, or Firm*—Browdy and Neimark

(57) ABSTRACT

A process for producing or separating trehalose and/or sugar alcohols from hydrogenated saccharide mixtures containing trehalose and sugar alcohols selected from the group consisting of sorbitol, maltitol, and maltotriitol, which comprises the steps of subjecting hydrogenated saccharide mixtures containing trehalose and the sugar alcohols to column chromatography using strong-acid cation exchange resins, and successively eluting and collecting a trehalose-rich fraction and a sugar alcohol-rich fraction in this order.

10 Claims, 2 Drawing Sheets

PROCESS FOR PRODUCING TREHALOSE AND SUGAR ALCOHOLS

BACKGROUND OF THE INVENTION

1. Field of the Invention

The present invention relates to a process for producing trehalose and sugar alcohols, more particularly, to a process for producing trehalose and/or sugar alcohols from a mixture of hydrogenated saccharides containing trehalose and sugar alcohols selected from the group consisting of sorbitol, maltitol, and maltotriitol; and to a process for separating trehalose and sugar alcohols.

2. Description of the Prior Art

Trehalose, a non-reducing disaccharide composed of two glucose molecules bound at their reducing groups, is widely distributed in nature; bacteria, fungus, algae, and insects. Comparing with sucrose as a representative sweetener, trehalose is much more stable than sucrose and is superior to sucrose on sweetening quality and mildness. Thus, trehalose are now being highly required as a substitute of sucrose in the fields of foods, cosmetics, and pharmaceutical industries.

There exist two different types of methods for producing trehalose when classified on materials; the first method is one which comprises contacting starch or partial starch hydrolysates thereof with a non-reducing saccharide forming enzyme and a trehalose-releasing enzyme as disclosed in Japanese Patent Kokai Nos. 143,876/95 and 213,283/95 applied by the same applicant as the present invention, and the second method is one which comprises contacting maltose with a maltose/trehalose converting enzyme as disclosed in Japanese Patent Kokai No. 170,977/95 applied by the same applicant as the present invention. The second method has the greatest merit that it easily produces trehalose with only a single enzyme if only the material maltose is in hand. In addition, such an enzymatic reaction is an equilibrium reaction, and this results in a formation of a saccharide mixture rich in both trehalose as a reaction product and maltose as a substrate.

However, no industrial and beneficial operation method for separating trehalose from such a saccharide mixture has been established. Even column chromatographies, used most effectively to separate saccharides, could not separate trehalose and maltose having the same molecular weight as trehalose due to the fact that most of the column chromatographies are to separate saccharides based on molecular differences in saccharides.

The above saccharide composition is a mixture of non-reducing and reducing saccharides, and this greatly lowers the utility value. As described above, the method using a maltose/trehalose converting enzyme has not yet actually been used as a method for producing trehalose or saccharide mixtures containing trehalose even if the method has an advantage that it produces trehalose with only a single enzyme.

The present inventors continued studying to improve the utility value of the above saccharide composition containing non-reducing and reducing saccharides. As a result, they found that when such saccharide mixtures are subjected to hydrogenation reaction under specific conditions, such reducing saccharides including maltose are effectively converted into sugar alcohols including maltitol without substantially decomposing trehalose as a non-reducing saccharide in the mixtures, resulting in producing a highly-useful saccharide in a relatively-high yield. Based on the finding, the present inventors established saccharides with lesser reducibility, its preparation and uses, and they disclosed them in Japanese Patent Kokai No. 73,482/96. Thus, it can be said that one of the problems residing in the method using a maltose/trehalose converting enzyme was overcome.

The method as disclosed in the above publication does aim at improving the utility value of the saccharide mixtures containing trehalose and reducing saccharides such as maltose, but does not aim at separating and producing useful saccharides including trehalose. For this reason, it is expected that the establishment of a process for producing trehalose from hydrogenated saccharide mixtures, which contain trehalose and sugar alcohols and are obtainable by the method disclosed in the above publication, would explore the way for an industrial production of trehalose in which a maltose/trehalose converting enzyme is used for producing trehalose. It is also greatly expected that when once established a process for producing sugar alcohols from the hydrogenated saccharide mixtures with a relatively-high yield, this would give a more effective utility to the method using a maltose/trehalose converting enzyme.

SUMMARY OF THE INVENTION

In view of the foregoing, the first object of the present invention is to provide a process for producing trehalose and/or sugar alcohols from hydrogenated saccharide mixtures containing trehalose and sugar alcohols.

The second object of the present invention is to provide a means for easily separating trehalose and sugar alcohols from hydrogenated saccharide mixtures containing trehalose and sugar alcohols.

The present inventors continued studying a process for effectively separating trehalose from hydrogenated saccharide mixtures containing trehalose and sugar alcohols such as maltitol. As a result, they unexpectedly and independently found that column chromatography using strong-acid cation exchange resins easily separates trehalose from the aforesaid hydrogenated saccharide mixtures. The fact that maltitol, a hydrogenated compound of maltose having approximately the same molecular weight as that of trehalose, can be separated from trehalose by the above column chromatography was an unexpected finding that upsets a common sense approved in this field. Based on this, the present inventors further studied and finally they established a preparation and separation methods that solve the above objects.

The present invention attains the first object of the invention by a process for producing trehalose and/or sugar alcohols, which comprises the steps of feeding hydrogenated saccharide mixtures containing trehalose and sugar alcohols selected from sorbitol, maltitol, and maltotriitol to column chromatography using strong-acid cation exchange resins, and collecting the resulting fractions rich in trehalose and/or sugar alcohols.

The present invention solves the second object of the invention by a separation method for trehalose and sugar alcohols, which is characterized in that it comprises the steps of feeding hydrogenated saccharide mixtures containing trehalose and sugar alcohols selected from sorbitol, maltitol, and maltotriitol to column chromatography using strong-acid cation exchange resins, and eluting a fraction rich in trehalose and a fraction rich in sugar alcohols in this order.

BRIEF DESCRIPTION OF THE ACCOMPANYING DRAWINGS

DETAILED DESCRIPTION OF THE INVENTION

Figure 1:
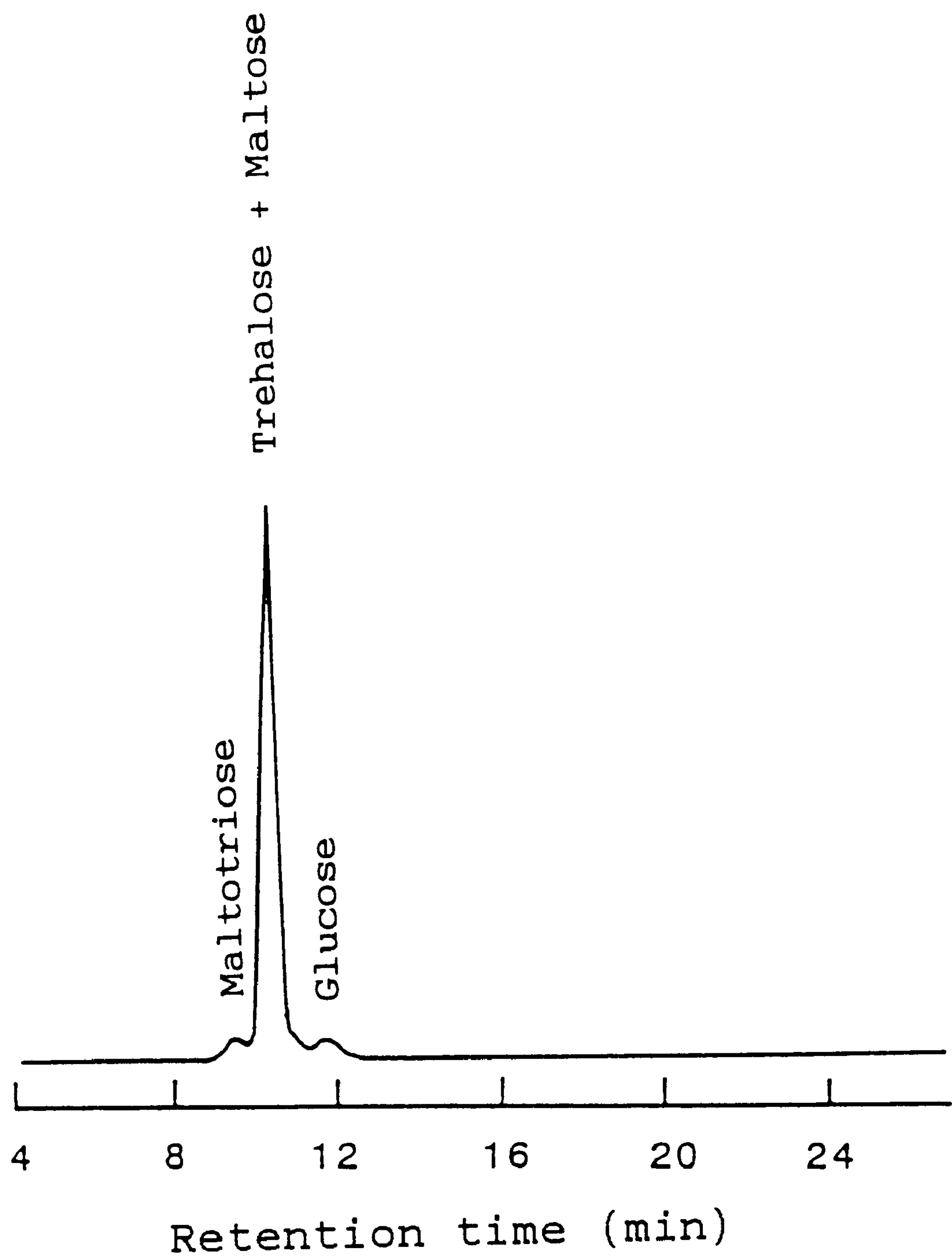
FIG. 1 is a chromatogram of an analytical result on HPLC using an alkaline-earth metal strong-acid cation exchange resin, applied to a saccharide mixture containing trehalose and reducing saccharides including at least maltose.

The present process for producing trehalose and/or sugar alcohols has the characters that it comprises the steps of feeding hydrogenated saccharide mixtures containing trehalose and sugar alcohols including at least maltitol to column chromatography using strong-acid cation exchange resins, and collecting the eluted fractions rich in trehalose and/or sugar alcohols. The present process might include the step of hydrogenating saccharide mixtures containing trehalose and reducing saccharides including at least maltose; In this case, the resulting hydrogenated products can be used as hydrogenated saccharide mixtures. Any hydrogenated saccharide mixture can be used in the present invention independently of its preparation method and saccharide composition, as long as it contains trehalose and a sugar alcohol(s) selected from sorbitol, maltitol, and maltotriitol. Any column chromatography can be used in the present invention as long as it uses strong-acid cation exchange resins.

The hydrogenated saccharide mixtures are obtainable by providing saccharide mixtures containing trehalose and reducing saccharides including at least maltose, and then hydrogenating the saccharide mixtures. The preparation for the saccharide mixtures is not specifically restricted, and more particularly the present process is easily applicable for the saccharide mixtures obtainable by contacting maltose or partial starch hydrolysates containing maltose with a maltose/trehalose converting enzyme, and for residual molasses obtainable after separating trehalose crystals from the saccharide mixtures. Referring to the maltose/trehalose converting enzyme and uses thereof are disclosed in detail in Japanese Patent Kokai Nos. 170,977/95, 263/96, and 149,980/96. In addition to the above saccharide mixtures, other saccharide mixtures usable in the present invention include those obtainable by a method, where maltose is converted into trehalose by the combination use of maltose- and trehalose-phosphorylases, as disclosed, for example, in Japanese Patent Kokai No. 216,695/83, and those obtainable by a method, where partial starch hydrolysates are contacted with a non-reducing saccharide-forming enzyme and a trehalose-releasing enzyme, as disclosed, for example, in Japanese Patent Nos. 143,876/95 and 213,283/95 applied by the same applicant as the present invention.

The hydrogenation method is not specifically restricted, and any method can be used in the present invention if only it can add hydrogen atom to aldehyde groups in reducing-saccharide molecules such as glucose, maltose, and maltotriose without decomposing trehalose in the saccharide mixtures. Examples of the hydrogenation method include a method that employs a chemical reduction reaction using sodium boron hydride and lithium aluminum hydride, and a method that employs an addition reaction using molecular hydrogen. In particular, the latter reaction conducted in the presence of appropriate catalysts, i.e. a method that employs contact hydrogenation is advantageously employed in the present invention. Any conventionally used metal-, metal oxide-, metal sulfate-, and metal complex-catalysts can be arbitrarily used in the present invention as such catalysts. More particularly, Raney catalyst, Urushihara nickel catalyst, and/or nickel boride catalyst can be mentioned. Among these catalysts, Raney nickel belonging to Raney catalyst has a satisfactorily-high reactivity and can be used satisfactorily.

The reaction conditions for the hydrogenation are appropriately chosen depending on the reaction systems and the type of catalysts to be used. For example, in the case of catalytic hydrogenation using Raney catalyst, saccharide mixtures are usually prepared into syrups with a concentration of 30 w/w % or higher, on a dry solid basis (d.s.b.), and preferably 40–75 w/w %, d.s.b., (the wording "w/w %" will be designated as "%" hereinafter, unless specified otherwise, and "the syrup concentration of solid content" is designated as "concentration"), followed by adding to the resulting mixtures at least one percent of Raney catalyst, and preferably, 2–15%, adjusting a hydrogen pressure of 20 $kg/cm^2$ or higher, and preferably 80–160 $kg/cm^2$, and increasing the temperature to 80° C. or higher, and preferably 90–150° C. The reaction apparatus used in the present invention includes any types of conventional ones that externally supply gas into tanks and control the pressure and temperature inside of the tanks to a desired level, and any batch-wise and continuous-type apparatuses can be arbitrarily used. Stirring-operable apparatuses can be satisfactorily used to accelerate reaction rate. The reaction systems under these conditions effectively promote hydrogenation of reducing saccharides such as glucose, maltose, and maltotriose without substantially decomposing trehalose. Because of this, the systems are most advantageously used in the present invention. In such conditions, the reducing saccharides in the saccharide mixtures are not substantially decomposed while their aldehyde groups are hydrogenated, resulting in effectively yielding sugar alcohols as useful saccharides as a merit.

Thus, hydrogenated saccharide mixtures, containing trehalose and sugar alcohols selected from sorbitol, maltitol, and maltotriitol, are obtained. The percentage (%) of each saccharide to solid contents in the hydrogenated saccharide mixtures (hereinafter, the percentage (%) of each saccharide to solid contents means "content" or "purity" thereof) is not specifically restricted, and usually the contents of trehalose and sugar alcohols are respectively 10–80% and 20–90%, and more preferably 30–80% and 20–70%, which are arbitrarily used in the present process.

If necessary, in the present process, the hydrogenated saccharide mixtures thus obtained can be treated with conventional filtration, centrifugation, decoloration, desalting, and/or concentration, and fed to column chromatography, followed by collecting the eluted fractions rich in trehalose and/or sugar alcohols. Examples of resins for separation to be packed in columns in the above column chromatography are those belonging to strong-acid cation exchange resins; any types of resins in an alkali metal- and alkaline-earth-metal-form can be arbitrarily used. Particularly, alkaline-earth-metal resins, that are composed of, as base materials, styrene/divinylbenzene polymers with a cross-linking of 2–8%, effectively separate trehalose and sugar alcohols. The cross-linking can be expressed by the percentage by weight of divinylbenzene to the total monomers in the material mixtures used for preparing the base materials. Any conventional batch-wise, pseudo-moving, and mono- and multi-column chromatographies can be used in the present invention.

The following are recommendable operation conditions used for applying batch-wise chromatography using strong-acid cation exchange resins which in the from of alkaline-earth metal, which comprise as a base material styrene/divinylbenzene polymers with a cross-linking of 2–8% are as follows: Feed to a column a syrupy hydrogenated saccharide mixture with a concentration of at least 30%, or preferably 40–75%, in a volume of 30 v/v % or lower, or preferably 1–15 v/v % to the resin volume, and feed to the column water, as a moving bed, heated to a temperature comparable to the column temperature, at an SV (space velocity) of 0.01–1, or preferably an SV of 0.05–0.5, while keeping the column temperature at 50° C. or higher, or preferably 60–90° C. The resin bed volume varies depending on the ingredients to be treated, and when required a daily output of about 10 tons, d.s.b., of hydrogenated saccharide mixtures as material saccharide solutions, it is preferably provided a column with a total gel bed-depth of at least about seven meters, or preferably 8–20 m, by injecting a resin to a column with a diameter of 3.5–5.5 m and cascading the plural number of such a column, if necessary. The best operation conditions used for column chromatography which employs other types of resins and operation modes can be set based on preliminary experiments conducted while examining the above conditions, and the contents of trehalose and/or sugar alcohols after analyzing the saccharide composition of each eluted fraction are determined by conventional methods such as thin-layer chromatography, gas chromatography, etc.

Fractions rich in trehalose and/or sugar alcohols are separatory collected from fractions eluted in the above column chromatography. Depending on uses, fractions to be collected can be chosen from among those with the desired ingredients in a higher level than the material saccharide solutions by analyzing the saccharide composition of all or each of eluted fractions, which are appropriately separated, to determine the content of the desired ingredients. In the chromatography, a fraction rich in trehalose is first eluted, and then a fraction rich in sugar alcohols is eluted. Fractions to be collected should be those rich in the objective ingredients, and particularly those with trehalose having a purity of at least 90%, can be advantageously used to obtain a relatively-high purity trehalose. If necessary, the resulting fractions can be treated with conventional filtration, centrifugation, decoloration, desalting, concentration, crystallization, separation, drying, pulverizing, and/or cutting to obtain the desired trehalose.

As described above, the present process facilitates an industrial-scale production of trehalose with a relatively-high purity trehalose, and more preferably with a purity of at least 90%, from hydrogenated saccharide mixtures containing trehalose and sugar alcohols. Application of the present process to hydrogenated saccharide mixtures, which are obtainable by crystallizing trehalose from saccharide mixtures containing trehalose and maltose and subjecting to hydrogenation reaction molasses remaining after the removal of the formed trehalose crystals, will also result in an increment of the yield of trehalose. Thus, the present process is extremely useful as a method for producing trehalose from hydrogenated saccharide mixtures obtained by hydrogenating saccharide mixtures produced by contacting maltose with a maltose/trehalose converting enzyme. The above process which further contains a step of hydrogenation reaction according to the present invention is extremely useful as a method for producing trehalose from saccharide mixtures produced by contacting maltose with a maltose/trehalose converting enzyme.

The high-purity trehalose thus obtained exhibits substantially no reducibility and has a mild sweetness, and therefore it can be widely used intact or in the form of a composition as a sweetener, sweetness-improving agent, stabilizer, filler, excipient, adjuvant, and filler. Such a trehalose in the above can be arbitrarily used in the fields of food, beverage, cosmetic, and pharmaceutical industries as disclosed, for example, in Japanese Patent Kokai Nos. 319,486/94, 213,283/95, 298,880/95, 66,187/96, 336,388/96, and 9,986/97, which are the applications of the same applicant as the present invention.

When the fractions collected from column chromatography are those rich in sugar alcohols, relatively-high purity non-reducing sugar alcohols such as sorbitol, maltitol, and maltotriitol can be easily obtained. More particularly, fractions with at least 90% maltitol, d.s.b., as sugar-alcohol rich fractions can be advantageously used to obtain a high-purity maltitol. The desired sugar alcohols can be produced by treating the resulting fractions with conventional treatments of filtration, centrifugation, decoloration, desalting, concentration, crystallization, separation, drying, pulverization, and/or cutting. The sugar alcohols thus obtained can be arbitrarily used as low-caloric sweeteners and low-dental-caries-inducing sweeteners. As disclosed, for example, in Japanese Patent Kokoku Nos. 13,699/72 and 26,817/92, sugar alcohols can be used in the fields of food, beverage, cosmetic, and pharmaceutical industries.

The present invention provides a method for separating trehalose and sugar alcohols from hydrogenated saccharide mixtures containing trehalose and sugar alcohols selected from sorbitol, maltitol, and maltotruitol. The present separation method is characterized in that it comprises fractionating hydrogenated sugar alcohols containing trehalose and sugar alcohols by column chromatography using strong-acid cation exchange resins in a manner such that fractions rich in trehalose and those rich in sugar alcohols are eluted from a column in this order. In the present separation method, any hydrogenated saccharide mixture can be used in the present invention as long as it contains trehalose and sugar alcohols such as sorbitol, maltitol, and maltotriitol independently of preparation method for and saccharide composition of the hydrogenated mixture. In particular, the aforesaid hydrogenated saccharide mixtures used in the present process can be satisfactorily used in the present separation method. Whenever used strong-acid cation exchange resins, any type of column chromatography can be used in the present invention. Particularly, the above column chromatography used in the present process can be advantageously used in the present separation method.

The present separation method can be advantageously used as a method for easily and quantitatively analyzing the content of trehalose in saccharide mixtures containing trehalose and reducing saccharides selected from glucose, maltose, and maltotriose; For example, by using conventional methods such as high-performance liquid chromatography as a column chromatography using strong-acid cation exchange resins, the saccharide mixtures are hydrogenated into hydrogenated saccharide mixtures, and then subjected to the present separation method, resulting in a quantitative detection of the trehalose in the saccharide mixtures with extreme-easiness. Thus, the present separation method is advantageously used in quality control for products containing trehalose and maltose, and is also used in the step control in which products containing trehalose and maltose are formed.

The following preferred examples explain the present invention in detail:

EXAMPLE 1

Ten parts by weight of "MALTOSE H", a maltose product with a purity of 94.0%, commercialized by Hayashibara Biochemical Laboratories Inc., Okayama, Japan, was dissolved in 40 parts by weight of water, and the solution was adjusted to a temperature of 15° C. and a pH of 7.0, admixed with two units/g maltose, d.s.b., of a maltose/trehalose converting enzyme derived from Pimelobacter sp. R48, FERM BP-4315, as disclosed in Japanese Patent Kokai No. 170,977/95 applied by the same applicant as the present invention, enzymatically reacted for 48 hours, and heated at 100° C. for 10 min to inactivate the remaining enzyme. The reaction mixture was in a conventional manner decolored with an activated charcoal and desalted for purification using ion-exchangers in H- and OH-form, and concentrated into an about 50%, syrupy saccharide mixture containing trehalose and maltose. According to the method as disclosed in Japanese Patent Kokai No. 170,977/95 applied by the same applicant as the present invention, the saccharide mixture was trimethylsilylated and analyzed on gas chromatography using a column packed with two percent of "SILICONE OV-17/CHROMOSORB W" commercialized by GL Sciences Inc., Tokyo, Japan (hereinafter abbreviated as "GLC"), revealing that the mixture contained about 65% trehalose, and about 26% maltose, as well as containing small amounts of glucose and maltotriose. A portion of the saccharide mixture was provided for the later described analysis, and the remaining mixture was placed in an autoclave, admixed with about 10% Raney nickel, d.s.b., heated to 90–120° C. under stirring conditions, and subjected to hydrogenation reaction by increasing the hydrogen pressure to 20–120 kg/cm$^2$. Thereafter, the Raney nickel was removed from the reaction mixture, and the remaining mixture was decolored and desalted for purification and adjusted to give a concentration of about 50%, to obtain a syrupy hydrogenated saccharide mixture.

Both the hydrogenated saccharide mixture thus obtained and the above portion of the saccharide mixture, which contains trehalose, maltose, glucose, and maltotriose, were respectively diluted to give a concentration of about two percent, followed by analyzing the dilutions on high-performance liquid chromatography (hereinafter abbreviated as "HPLC") using and under the conditions of: "CCPD SYSTEM", an apparatus for HPLC commercialized by Tosoh Corporation, Tokyo, Japan; a column for analysis packed with "MCI GEL CK08EC, Ca$^{++}$-form", a cross-linking of 8%, a column size of 8.0 mm in diameter and 300 mm in length, commercialized by Mitsubishi Chemical Industries Ltd., Tokyo, Japan; a flow rate of 0.6 ml/min as a water for moving phase; and a differential refractometer as a detector. The analytical results of the saccharide mixture and the hydrogenated saccharide mixture are respectively shown in FIGS. 1 and 2.

Figure 2:
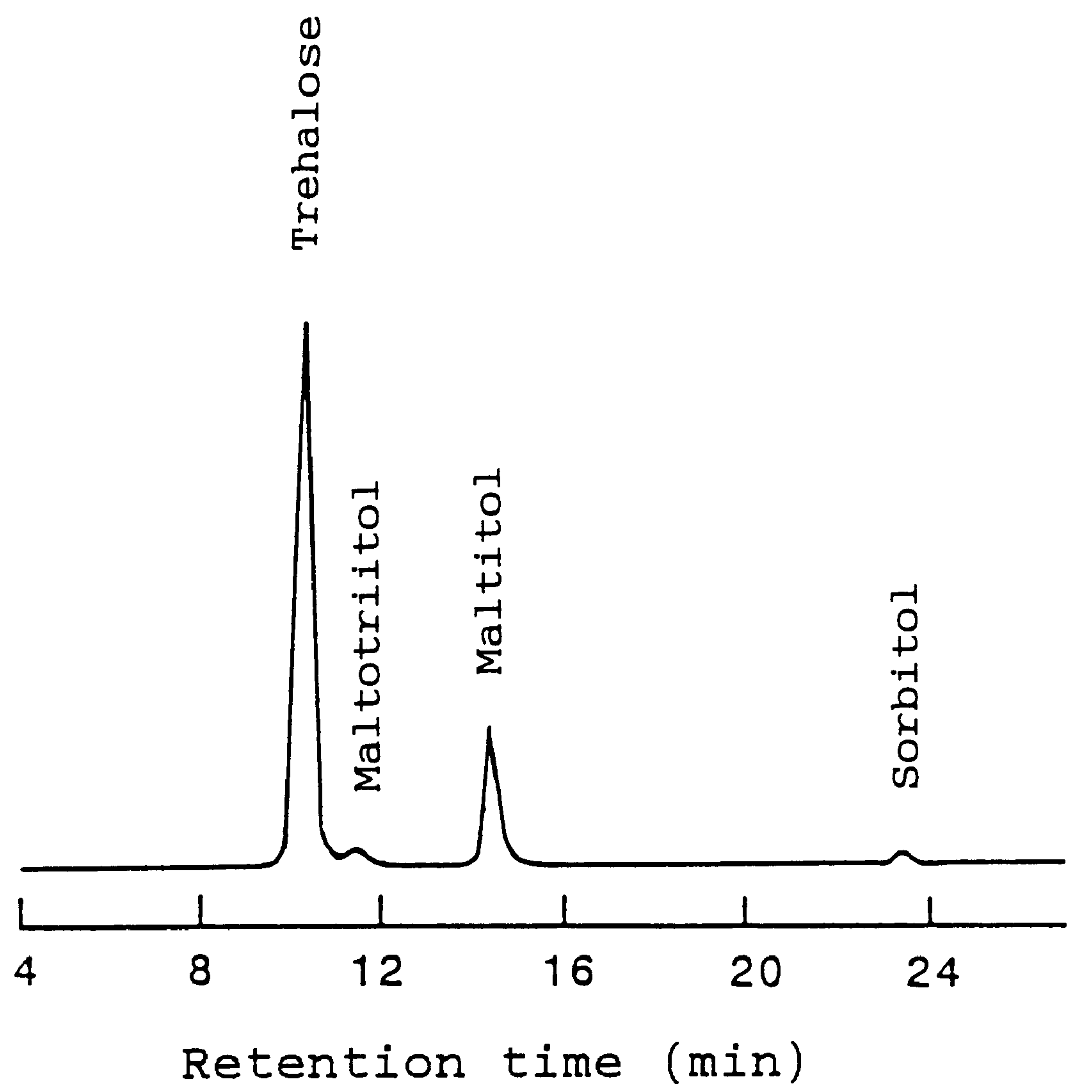
FIG. 2 is a chromatogram of an analytical result on HPLC using an alkaline-earth metal strong-acid cation exchange resin, applied to a hydrogenated saccharide mixture containing trehalose and sugar alcohols including at least maltitol.

As evident from FIG. 1, it was found that trehalose and maltose in the saccharide mixture were hardly separated, and as evident from FIG. 2, it was also found that trehalose, contained in the hydrogenated saccharide mixture, was easily separated from maltitol as well as sorbitol and maltotriitol. Based on the result in FIG. 2, it was revealed the present separation method using HPLC easily and quantitatively detects trehalose. The saccharide composition determined from the result is in Table 1.

TABLE 1

| Component | Retention time (min) | Percentage (%) |
|---|---|---|
| Trehalose | 10.2 | 65.4 |
| Maltotriitol | 11.4 | 5.3 |
| Maltitol | 14.4 | 25.5 |
| Sorbitol | 23.4 | 3.8 |

The hydrogenated saccharide mixture obtained in the above was fed to column chromatography using "50W X4, Ca$^{++}$-form", a strong-acid alkaline-earth metal cation exchange resin with a cross-linking of 4%, commercialized by The Dow Chemical Co., Midland, Mich., USA; The resin was packed in four jacketed-stainless-steel columns with three centimeters in diameter, and these columns were cascaded in series to give a total gel-bed depth of about four meters. The columns were fed with a hydrogenated saccharide mixture in a volume of 5 v/v % to the resin by volume while the inner column temperature was keeping at 80° C., and fed with hot water heated to 80° C. at SV 0.15. In the order of elution, fractions with a trehalose content of at least 90%, were first collected, and then the successively-eluted fractions containing maltotriitol, maltitol, and sorbitol were removed. The yield of solid contents in this step was about 50%, d.s.b.

The fraction rich in trehalose was purified using ion-exchanges in H- and OH-form and concentrated to give a concentration of about 76%, and in a conventional manner the concentrate was placed in a crystallizer and admixed by stirring with an about one percent, d.s.b., of crystalline trehalose hydrate to crystallize trehalose. The resulting massecuite was separated, followed by washing the resulting crystals by spraying a small amount of water to obtain crystalline trehalose hydrate. The yield of trehalose from the trehalose-rich fraction obtained in column chromatography was about 70%, d.s.b. HPLC analysis using the above column packed with "MCI GEL CK08EC, Ca$^{++}$-form" revealed that the product had a trehalose purity of 99.2%. Since the product shows substantially no reducibility and has a mild sweetness, it can be arbitrarily used in food products, cosmetics, and pharmaceuticals as a taste-improving agent, stabilizer, filler, excipient, adjuvant, and diluent.

EXAMPLE 2

In accordance with the method in Example 1, 10 parts by weight of "MALTOSE HHH", a maltose product with a purity of 99.5%, commercialized by Hayashibara Biochemical Laboratories, Inc., Okayama, Japan, as a material, was enzymatically reacted with a maltose/trehalose converting enzyme derived from Pimelobacter sp. R48, FERM BP-4315. The reaction mixture was purified by decoloring with an activated charcoal and desalting with ion-exchange resins in H- and OH-form, and concentrated to give a concentration of about 78%. Thus a syrupy saccharide mixture was obtained, then placed in a crystallizer, and in accordance with a method in Example 1 crystalline trehalose hydrate was crystallized to obtain a massecuite which was then separated into an about three parts by weight of crystalline trehalose hydrate with a purity of about 99.8%. The syrup formed as molasses after the separation was adjusted to give a concentration of about 50%, and the concentrate was subjected to hydrogenation reaction in accordance with the method in Example 1 and further purified to obtain a syrupy hydrogenated saccharide mixture. HPLC analysis using the above column packed with "MCI GEL CK08EC, Ca$^{++}$-form" revealed that the mixture had about 67% trehalose, about 29% maltitol, and a small amount of sorbitol.

The hydrogenated saccharide mixture was subjected to column chromatography using "CG6000, $Ca^{++}$-form, a cross-linking of 6%", an alkaline-earth metal strong-acid cation exchange resin commercialized by Japan Organo Co., Ltd., Tokyo, Japan; Four jacketed-stainless steel columns, with an inner diameter of 5.4 cm, were packed with the resin and cascaded in series to give a total column gel-bed depth of 20 m. The above hydrogenated saccharide mixture was fed to the columns in a volume of 5 v/v % to the resin by volume, followed by feeding as a moving phase water heated to 80° C. at SV 0.15 and successively collecting a trehalose-rich fraction with a trehalose content of at least 90%, and a maltitol-rich fraction with a maltitol content of at least 90%. The yields of solid contents in these fractions, collected from the material hydrogenated saccharide mixture, were respectively about 55% and about 18%, d.s.b.

The trehalose-rich fraction thus obtained was purified by desalting using ion-exchange resins in H- and OH-form and concentrated to give a concentration of about 83%. The concentrate was admixed with about two percent of crystalline trehalose hydrate as a seed to crystallize trehalose under stirring conditions, and the crystals were transferred to an aluminum container, and aged at ambient temperature to form a block. The resulting block was cut, pulverized, and dried in vacuo to obtain a powdery crystalline trehalose hydrate. The yield of solid contents in the step was about 94%, d.s.b. The product had a trehalose purity of about 94%. Since the product shows substantially no reducibility and has a mild sweetness, it can be arbitrarily used in food products, cosmetics, and pharmaceuticals as a sweetener, taste-improving agent, stabilizer, filler, excipient, adjuvant, and diluent.

In accordance with the method used for treating the above trehalose-rich fraction, a crystalline powder with a maltitol purity of about 93%, was obtained from the above maltitol-rich fraction except that the maltitol-rich fraction was previously concentrated to give a concentration of about 90%. The yield of solid contents in the step was about 90%, d.s.b. The product shows substantially no reducibility and has a sharpened sweetness. Furthermore, since the product has a relatively-low calorific value and a relatively-low-dental-caries-inducibility, it can be advantageously used in food products, cosmetics, and pharmaceuticals.

EXAMPLE 3

To a 15% starch suspension (pH 5.5) was added two units per g starch, d.s.b., of "SPITASE HS", an α-amylase specimen commercialized by Nagase Biochemicals, Ltd., Kyoto, Japan, then the suspension was heated to gelatinize and liquefy the contents under stirring conditions, followed by autoclaving the resulting mixture at 120° C. for 20 min and adjusted to give a temperature of 50° C. and a pH of 5.0. The mixture thus obtained was mixed with 500 units/g starch, d.s.b., of an isoamylase specimen commercialized by Hayashibara Biochemical Laboratories, Inc., Okayama, Japan, and 20 units/g starch, d.s.b., of a β-amylase specimen commercialized by Nagase Biochemicals, Ltd., Kyoto, Japan, and enzymatically reacted for 24 hours. The reaction mixture contained about 92% maltose, d.s.b. The mixture was heated at 100° C. for 20 min, adjusted to a temperature of 50° C. and a pH of 7.0, and admixed with 1.5 units/g dry solids of a maltose/trehalose converting enzyme derived from *Thermus aquaticus*, ATCC 33923, as disclosed in Japanese Patent Kokai No. 170,977/95, and enzymatically reacted for 72 hours.

The reaction mixture was incubated at 95° C. for 10 min and cooled, and in a conventional manner the resulting mixture was purified by decoloring using an activated charcoal and by desalting using ion-exchange resins in H- and OH-form, and concentrated to give a concentration of about 50%. Thus a syrupy saccharide mixture containing trehalose and maltose was obtained. GLC analysis described in Example 1 revealed that the saccharide mixture contained about 64% trehalose, about 25% maltose, and small amounts of glucose and maltotriose.

The above saccharide mixture was placed in an autoclave, admixed with 10% Raney nickel, d.s.b., and heated to 90–120° C., and hydrogenated by increasing the hydrogen pressure to 20–120 $kg/cm^2$ under stirring conditions, followed by removing the Raney nickel and purifying the mixture by decoloring and desalting in a conventional manner. The purified solution was concentrated into an about 50% syrupy hydrogenated mixture, d.s.b. HPLC analysis described in Example 1 revealed that the hydrogenated saccharide mixture was contained about 64% trehalose, about 25% maltitol, and small amounts of other sugar alcohols such as sorbitol and maltotriitol.

The hydrogenated saccharide mixture was subjected to column chromatography using "CG6000, $Ca^{++}$-form, a cross-linking of 6%", an alkaline-earth metal strong-acid cation exchange resin commercialized by Japan Organo Co., Ltd., Tokyo, Japan; Four jacketed-stainless steel columns, with an inner diameter of 5.4 cm, were packed with the resin and cascaded in series to give a total column gel-bed depth of 20 m. The above hydrogenated saccharide mixture was fed to the columns in a volume of 5 v/v % to the resin by volume, followed by feeding as a moving phase water heated to 80° C. at SV 0.15 and successively collecting a trehalose-rich fraction with a trehalose content of at least 90%, and a maltitol-rich fraction with a maltitol content of at least 90%. The yields of solid contents in these fractions, collected from the material hydrogenated saccharide mixture, were respectively about 50% and about 15%, d.s.b.

The trehalose-rich fraction thus obtained was purified by desalting using ion-exchange resins in H- and OH-form and concentrated to give a concentration of about 70%. The concentrate was admixed with about two percent, d.s.b., of crystalline trehalose hydrate as a seed to crystallize trehalose to obtain a massecuite with a crystallinity of about 45%. The massecuite was subjected to spray drying in a manner such that it was sprayed at a high-pressure of 150 $kg/cm^2$ from a nozzle equipped on the top of a spray dryer while air heated to 85° C. was allowed to blow to the contents from the upper part of the spray dryer, and collected over a wire-netting transfer conveyer equipped on the lower part of the spray dryer, followed by collecting crystalline powder collected on the conveyer while the contents were gradually being put out from the ageing tower and being blown by air heated to 45° C. The crystals thus obtained were injected to an ageing tower and aged therein for 10 hours while hot air was ventilating to obtain a powdery crystalline trehalose hydrate. The yield of solid contents in the step was about 90%, d.s.b. Since the product has a trehalose purity of about 95%, an insubstantial reducibility, and a mild taste, it can be arbitrarily used in food products, cosmetics, and pharmaceuticals as a sweetener, taste-improving agent, stabilizer, filler, excipient, adjuvant, and diluent.

The maltitol-rich fraction obtained in the above was treated in accordance with the above method for treating the trehalose-rich fraction to obtain a crystalline powder with a maltitol purity of about 93%, except that the maltitol-rich fraction was previously concentrated to give a concentration of about 80%. The yield of solid contents in the step was about 85%, d.s.b. Since the product shows substantially no reducibility, a sharpened sweetness, and a relatively-low-dental-caries-inducibility, it can be arbitrarily used in food products, cosmetics, and pharmaceuticals.

EXAMPLE 4

According to the method in Example 3, an about 50% hydrogenated saccharide mixture containing about 64% trehalose was obtained, and then fed to a pseudo-moving bed column chromatography using "CG6000, $Ca^{++}$-form, a cross-linking of 6%", an alkaline-earth metal strong-acid cation exchange resin commercialized by Japan Organo Co., Ltd., Tokyo, Japan; A pseudo-moving bed column chromatograph, wherein the on/off of valves for the inlets and outlets as mentioned below was computerized, was provided by cascading 10 jacketed-stainless-steel-columns with a diameter of 13 cm and a length of 1.6 m each, providing inlets for feeding a material saccharide and a moving phase on the upper part of each column, and providing outlets for collecting a trehalose-rich fraction and a sugar alcohol-rich fraction on the lower part of each column. The column chromatography was operated under the conditions of that the inner column temperature was kept at 80° C., the feeding rate of the above hydrogenated saccharide mixture as the material saccharide was set to 6.8 l/hr, the feeding rate of the water as the moving phase was set to 20 l/hr, and the recovering rate for the trehaose-rich fraction was set to 16 l/hr. The columns were respectively switched at a time interval of 21 min. The pseudo-moving bed column chromatography yielded a trehalose-rich fraction containing at least 90% trehalose, d.s.b., and a sugar alcohol-rich fraction containing at least 90% sugar alcohols comprising sorbitol, maltitol, and maltotriitol, d.s.b. The yields of solid contents in these fractions from the hydrogenated saccharide mixture were respectively about 55% and about 18%, d.s.b. Similarly as in Example 3, the trehalose-rich fraction was crystallized and spray-dried into a powdery crystalline trehalose hydrate. Since the product contains about 95% trehalose and shows substantially no reducibility, and a mild sweetness, it can be arbitrarily used in food products, cosmetics, and pharmaceuticals as a sweetener, taste-improving agent, stabilizer, filler, excipient, adjuvant, and diluent. The sugar alcohol-rich fraction thus obtained was in a conventional manner purified by desalting and concentrated to give a concentration of about 70%, resulting in a syrup rich in sugar alcohols. Since the product shows substantially no reducibility, a sharpened sweetness, a relatively-low calorific value, and a relatively-low dental-caries-inducibility, it can be arbitrarily used in food products, cosmetics, and pharmaceuticals.

As described above, the present invention was made based on a novel self-finding of that the separation of trehalose from saccharide mixtures containing trehalose and reducing saccharides such as maltose, which has been deemed impossible, is easily attained by applying column chromatography using strong-acid cation exchange resins to hydrogenated saccharide mixtures, which contain trehalose and sugar alcohols such as maltitol, obtained by hydrogenating the saccharide mixtures containing the reducing saccharides. The present inventors established the present process for producing trehalose and/or sugar alcohols, which comprises the steps of feeding hydrogenated saccharide mixtures containing trehalose and sugar alcohols selected from the group consisting of sorbitol, maltitol, and maltotruitol to column chromatography using strong-acid cation exchange resins; eluting a trehalose-rich fraction and a sugar alcohol-rich fraction in this order; and collecting the trehalose-rich and/or sugar alcohol-rich fractions. When applied to hydrogenated saccharide mixtures obtained by hydrogenating saccharide mixtures containing trehalose and reducing saccharides such as glucose, maltose, and maltotriose, the present process strongly facilitates an industrial production of trehalose and/or sugar alcohols from the hydrogenated saccharide mixtures. The process according to the present invention, which further contains a step of hydrogenating saccharide mixtures containing trehalose and reducing saccharides including maltose, extremely facilitates an industrial production of trehalose and/sugar alcohols from the hydrogenated saccharide mixtures.

The establishment of the present process explores a new way that easily provides trehalose as a non-reducing saccharide and sugar alcohols on an industrial scale. Thus it is unfathomable the influence of the present invention on the field of food products including sweeteners and on the fields of cosmetic and pharmaceutical industries, as well as those of agricultural-, fishery-, and animal-industries, and chemical industries.

While there has been described what is at present considered to be the preferred embodiments of the invention, it will be understood the various modifications may be made therein, and it is intended to cover in the appended claims all such modifications as fall within the true spirits and scope of the invention.

We claim:

1. A process for producing trehalose or a sugar alcohol, which comprises the steps of:

providing a saccharide mixture comprising trehalose and maltose;

hydrogenating the resulting saccharide mixture to form a hydrogenated saccharide mixture comprising trehalose and maltitol as a sugar alcohol;

adjusting said hydrogenated saccharide mixture to give a concentration of at least 30 w/w %;

subjecting the hydrogenated saccharide mixture to column chromatography using a strong acid cation exchange resin made of a styrene/divinylbenzene polymer as a base material and which has a cross-linking of 2–8%; and collecting a fraction rich in said trehalose or said sugar alcohol.

2. The process of claim 1, wherein said hydrogenated saccharide mixture contains said trehalose and said sugar alcohol in respective amounts of 10–80 w/w % and 20–90 w/w %, on a dry solid basis.

3. The process of claim 1, wherein said strong-acid cation exchange resin is in an alkali metal form or an alkaline-earth metal form.

4. The process of claim 1, wherein said column chromatography is carried out by eluting the fraction rich in said trehalose and the fraction rich in said sugar alcohol in this order.

5. The process of claim 1, which collects a fraction, as the fraction rich in said trehalose, that contains at least 90 w/w % trehalose, on a dry solid basis.

6. The process of claim 1, which collects a fraction, as the fraction rich in said sugar alcohol, that contains at least 90 w/w % maltitol, on a dry solid basis.

7. The process of claim 1, which further contains a step of hydrogenating a saccharide mixture containing trehalose and a reducing saccharide selected from the group consisting of glucose, maltose, and maltotriose, and which uses the resulting hydrogenated product as the hydrogenated saccharide mixture.

8. The process of claim 7, wherein said saccharide mixture is one which is obtainable by contacting starch or maltose with one or more enzymes.

9. The process of claim 8, wherein said enzymes are a non-reducing saccharide forming enzyme, trehalose-releasing enzyme, maltose/trehalose converting enzyme, and maltose- and trehalose-phosphorylases.

10. A method for separating trehalose from a sugar alcohol, which comprises the steps of:

providing a saccharide mixture comprising trehalose and maltose;

hydrogenating the resulting saccharide mixture to form a hydrogenated saccharide mixture comprising trehalose and maltitol as a sugar alcohol;

adjusting said hydrogenated saccharide mixture to give a concentration of at least 30 w/w %;

subjecting hydrogenated saccharide mixture to column chromatography using a strong-acid cation exchange resin made of a styrene/divinylbenzene polymer as a base material and which has a cross-linking of 2–8%; and eluting a fraction rich in said trehalose and a fraction rich in said sugar alcohol in this order.

* * * * *

UNITED STATES PATENT AND TRADEMARK OFFICE

CERTIFICATE OF CORRECTION

PATENT NO. : 6,200,783 B1
DATED : March 13, 2001
INVENTOR(S) : Hiroto Chaen et al.

It is certified that error appears in the above-identified patent and that said Letters Patent is hereby corrected as shown below:

Title page, column 1,
Line 30, delete "10-297957" and insert therefor -- 9-297957 --.

Signed and Sealed this

Twenty-third Day of October, 2001

Attest:

Nicholas P. Godici

NICHOLAS P. GODICI

*Attesting Officer* *Acting Director of the United States Patent and Trademark Office*